United States Patent
Pinori et al.

(10) Patent No.: US 7,329,689 B2
(45) Date of Patent: Feb. 12, 2008

(54) MONOHYDRATE HYDROCHLORIDE OF THE 4-HYDROXYCARBAMOYL-PHENYL)-CARBAMIC ACID (6-DIETHYLAMINOMETHYL-NAPHTALEN-2-YL) ESTER

(75) Inventors: Massimo Pinori, Paderno d'Adda (IT); Paolo Mascagni, Villasanta (IT)

(73) Assignee: Italfarmaco SpA, Milano (IT)

( * ) Notice: Subject to any disclaimer, the term of this patent is extended or adjusted under 35 U.S.C. 154(b) by 7 days.

(21) Appl. No.: 11/149,548

(22) Filed: Jun. 10, 2005

(65) Prior Publication Data
US 2005/0245604 A1  Nov. 3, 2005

Related U.S. Application Data

(63) Continuation of application No. PCT/IT2004/000003, filed on Jan. 8, 2004.

(30) Foreign Application Priority Data
Jan. 17, 2003 (IT) .................. MI2003A0063

(51) Int. Cl.
*C07C 261/00* (2006.01)
*A61K 31/27* (2006.01)

(52) U.S. Cl. .............. 514/485; 514/484; 560/33; 560/132

(58) Field of Classification Search ............ 560/33, 560/132; 514/485, 484
See application file for complete search history.

(56) References Cited

U.S. PATENT DOCUMENTS 6,034,096 A    3/2000  Bertolini et al.

*Primary Examiner*—Taylor Victor Oh
(74) *Attorney, Agent, or Firm*—Nixon & Vanderhye

(57) ABSTRACT

A compound having formula (I) and a process for the preparation thereof are described.

2 Claims, 3 Drawing Sheets

MONOHYDRATE HYDROCHLORIDE OF THE 4-HYDROXYCARBAMOYL-PHENYL)-CARBAMIC ACID (6-DIETHYLAMINOMETHYL-NAPHTALEN-2-YL) ESTER

This application is a continuation of Application No. PCT/IT2004/000003, filed 8 Jan., 2004, the entire content of which is hereby incorporated by reference in this application.

The present invention relates to a derivative of hydroxamic acid having anti-inflammatory activity.

PRIOR ART

Hydrochloride of (6-diethylaminomethyl-naphthalen-2-yl)-methyl ester of (4-hydroxycarbamoylphenyl)-carbamic acid (II)

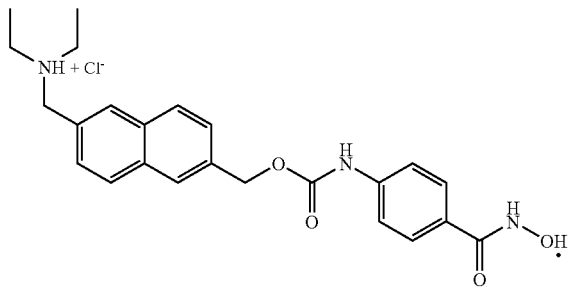

(II)

has been described in U.S. Pat. No. 6,034,096 as a derivative of hydroxamic acid having anti-inflammatory and immunosuppressive activity, probably owing to the ability thereof to inhibit the production of pro-inflammatory cytokines. This compound is obtained according to Example 12 of the above-mentioned patent as an anhydrous, amorphous, hygroscopic, deliquescent solid which is difficult to handle.

STATEMENT OF INVENTION

The subject-matter of the present invention is the crystalline form of monohydrous hydrochloride of (6-diethylaminomethyl-naphthalen-2-yl)-methyl ester of (4-hydroxycarbamoylphenyl)-carbamic acid (I).

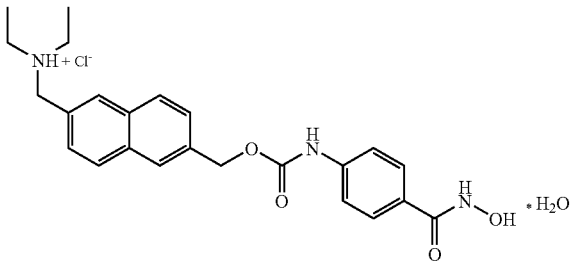

(I)

This form is particularly advantageous from the industrial perspective because it is stable and simpler to handle than the anhydrous and amorphous form described above.

The monohydrate (I) is obtained by means of a process which comprises the following steps:
a) reaction of 4-(6-diethylaminomethyl-naphthalen-2-ylmethoxycarbonylamino)benzoic acid with thionyl chloride in tetrahydrofuran as the solvent to provide the corresponding acid chloride;
b) reaction of the acid chloride with an aqueous solution of hydroxylamine in tetrahydrofuran as the solvent and precipitation of the hydrochloride by addition of hydrochloric acid;
c) dissolution of the hydrochloride obtained in the preceding step in a solution of sodium bicarbonate;
d) extraction of the solution with a mixture of tetrahydrofuran and ethyl acetate;
e) precipitation of the monohydrous hydrochloride by addition of 37% HCl.

The presence of solvation water has been confirmed by means of DSC analysis, which shows a desolvation endotherm between 80 and 120° C. (FIG. 1), and by means of thermogravimetric analysis (FIG. 2), which shows a loss of 3.3% between 40 and 120° C., owing to the loss of the crystallisation solvent. The crystalline form of the product is confirmed by X-ray analysis (FIG. 3).

The present invention further relates to pharmaceutical compositions containing compound (I); these compositions can be in the form of capsules, pills, coated pills, creams, ointments or vials for oral, intramuscular or intravenous administration.

The compound of formula (I) is contained alone or in admixture with conventional carriers or excipients, for example, those described in Remington's Pharmaceutical Sciences Handbook, XVII ed., Mack Pub., N.Y., U.S.A.

Figure 1:
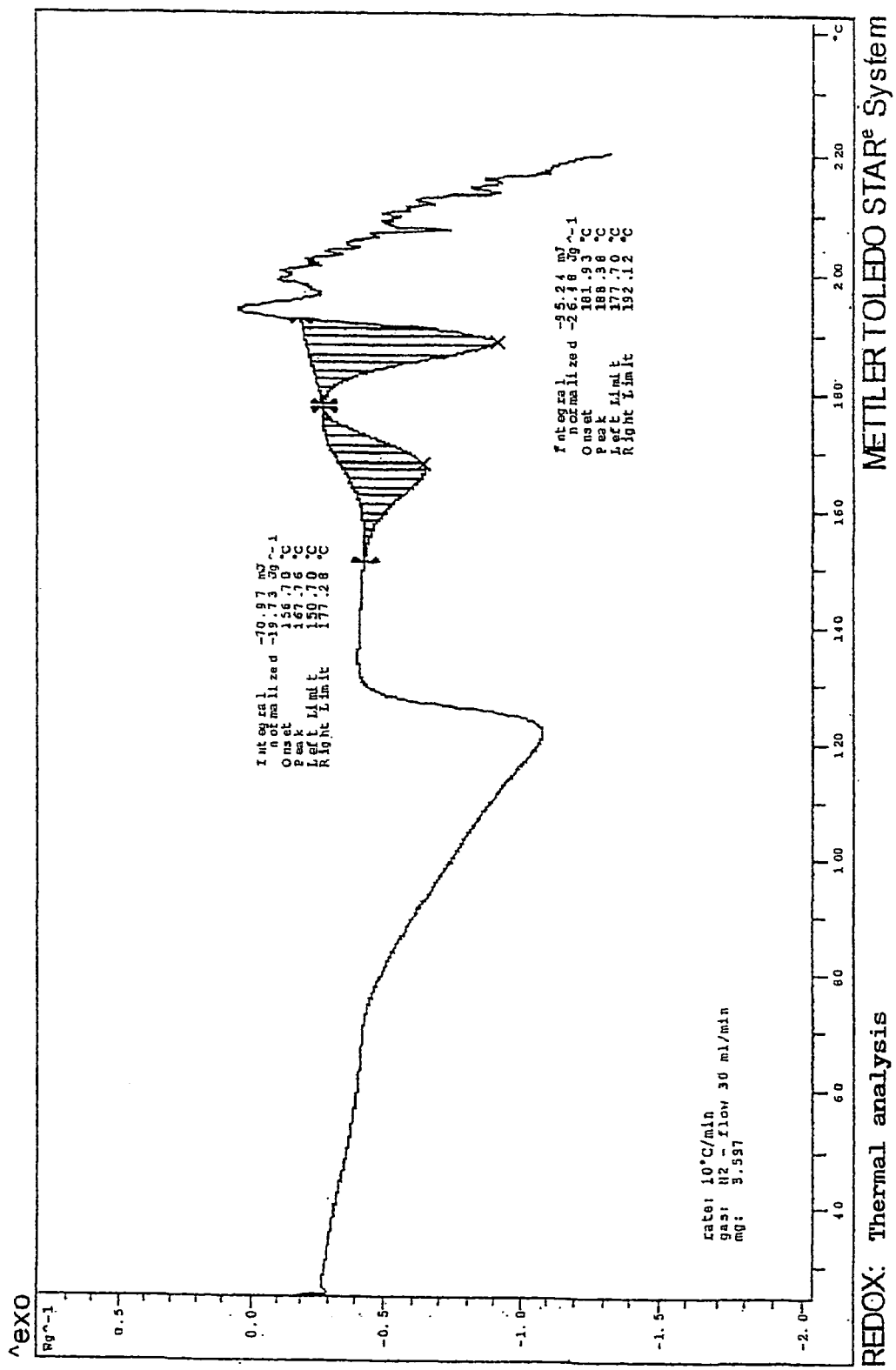
FIG. 1. DSC analysis of compound (I)
Figure 2:
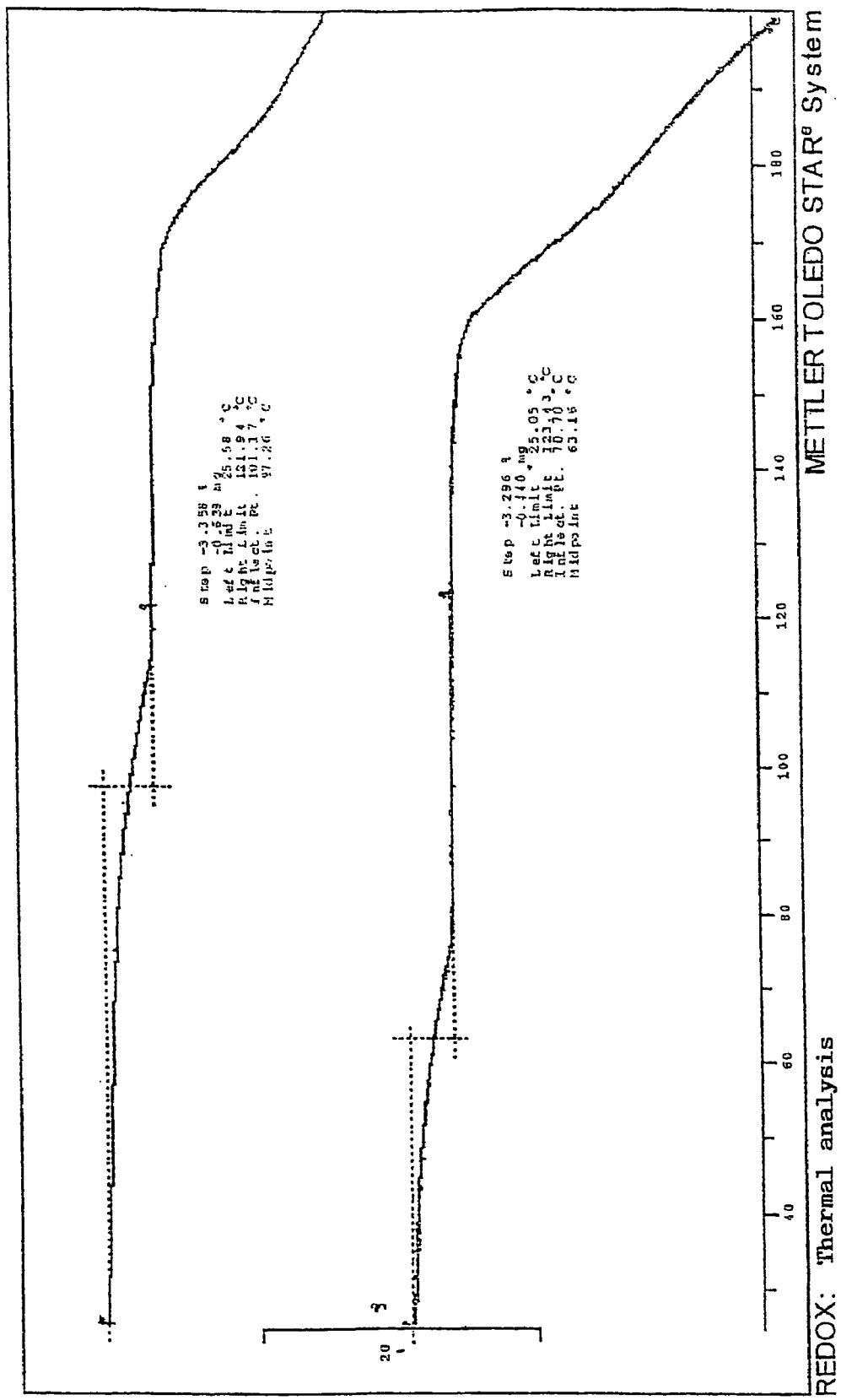
FIG. 2. thermogravimetric analysis of two samples of compound (I)

The invention will now be explained below in greater detail with reference to the following Example.

EXAMPLE

Materials and Methods

The differential scanning calorimetry (DSC) and thermogravimetric analysis (TGA) were carried out with a Mettler TA8000 instrument provided with a cell DSC821/700 and by a TG 50 thermobalance under the following conditions:
gas: nitrogen 20-30 ml/min.;
containers: open capsules of aluminium;
heating rate: 10° C./min.;
evaluation of the thermal events by means of "Star System" software.

The 4-(6-diethylaminomethyl-naphthalen-2-ylmethoxycarbonylamino)-benzoic acid can be prepared as described in Example 12, point C, of U.S. Pat. No. 6,034,096.

The acid (1.22 kg, 3 moles) was suspended in THF (19 l) and the mixture was agitated under nitrogen over night at ambient temperature. The mixture was then cooled to 0° C. and thionyl chloride (0.657 l, 9 moles) was added slowly, still under nitrogen, with the temperature being maintained below 10° C. The reaction mixture was heated under reflux for 60 minutes, DMF (26 ml) was added and the mixture was further heated under reflux for 60 minutes.

The solvent was evaporated under vacuum, toluene was added to the residue and was then evaporated. This operation was repeated twice, then the residue was suspended in THF (11.5 l) and the mixture was cooled to 0° C.

The mixture was then poured into a cold solution of hydroxylamine (50% aq., 1.6 l, 264 moles) in 5.7 l of water. The mixture was then cooled to ambient temperature and agitated for 30 minutes. 6M HCl was added until pH 2 was reached and the mixture was partially evaporated under vacuum in order to eliminate most of the THF. The solid was filtered, washed repeatedly with water and dissolved in a solution of sodium bicarbonate (2.5%, 12.2 l). The solution was extracted with 18.6 l of a mixture of THF and ethyl acetate (2:1 v/v). 37% HCl (130 ml) were added to the organic layer in order to precipitate the monohydrate of the (6-diethylaminomethyl-naphthalen-2-yl)-methyl ester hydrochloride of the (4-hydroxycarbamoyl-phenyl)-carbamic acid. If necessary, this operation can be repeated several times to remove any residues of the original acid.

Finally, the solid was dried under vacuum (approximately 30 mbar, 50° C.), producing 0.85 kg (60%) of compound (I).

HPLC purity: 99.5%; water content (Karl Fischer method): 3.8%; (argentometric) assay: 99.8%.

| | Elemental analysis | | | |
|---|---|---|---|---|
| | C % | H % | Cl % | N % |
| Calculated for $C_{24}H_{30}ClN_3O_5$ | 60.56 | 6.35 | 7.45 | 8.83 |
| Found | 61.06 | 6.48 | 7.48 | 8.90 |

The invention claimed is:

1. Monohydrous hydrochloride of (6-diethylaminomethyl-naphthalen-2-yl)-methyl ester of (4-hydroxycarbamoylphenyl)-carbamic acid of formula (I)

Figure 3:
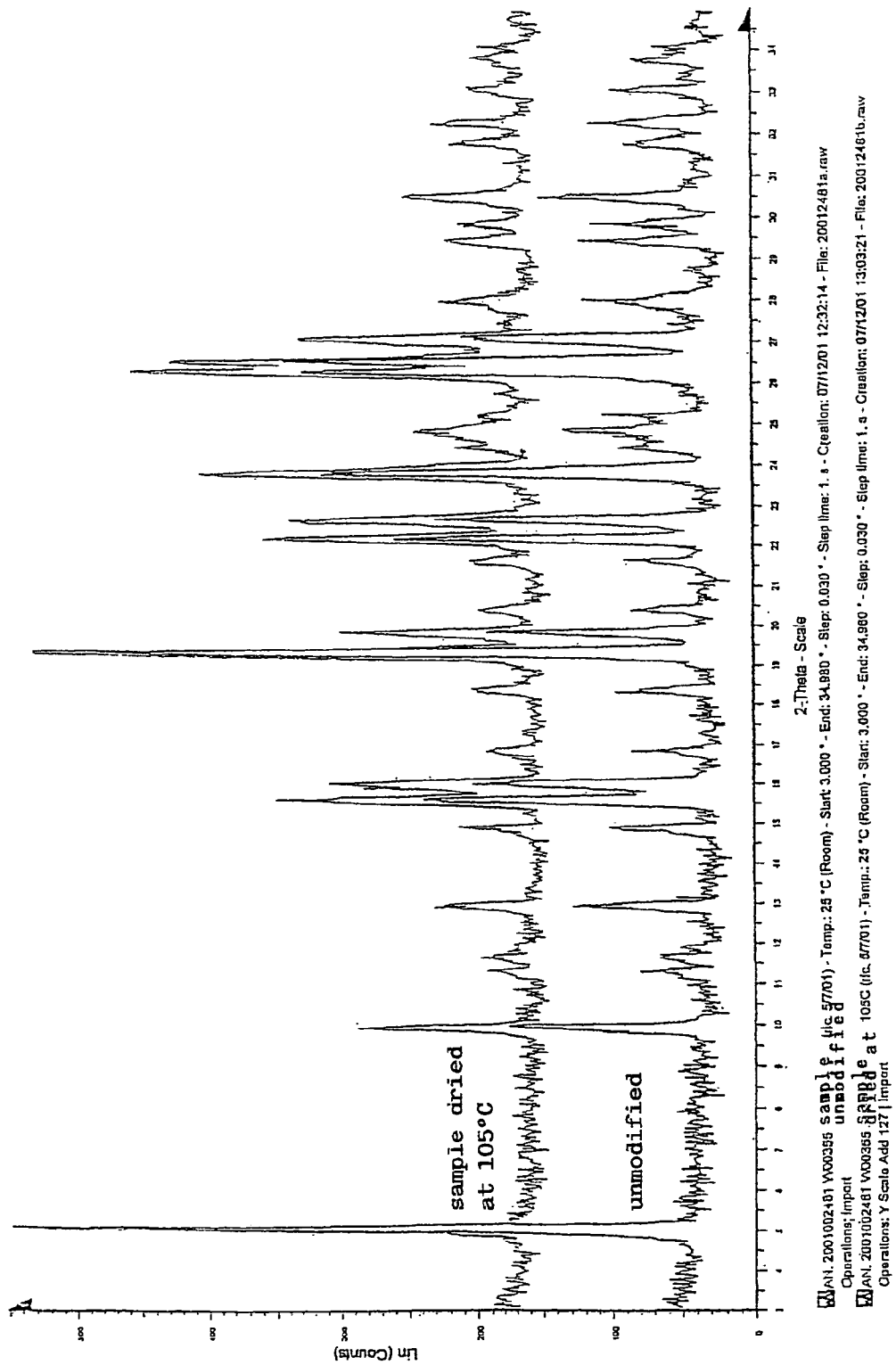
FIG. 3. diffractometric analysis of compound (I) unmodified and after drying.

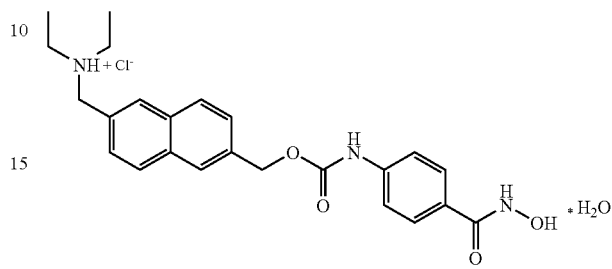

in crystalline form having the diffraction spectrum shown in FIG. 3.

2. A pharmaceutical composition comprising the compound of claim 1.

* * * * *